United States Patent [19]

Beller et al.

[11] Patent Number: 5,475,176
[45] Date of Patent: Dec. 12, 1995

[54] PROCESS FOR PREPARING VINYL-SUBSTITUTED AROMATIC COMPOUNDS FROM ARYLAMINES

[75] Inventors: Matthias Beller, Niedernhausen; Heinz Strutz, Frankfurt am Main, both of Germany

[73] Assignee: Hoechst Aktiengesellschaft, Frankfurt, Germany

[21] Appl. No.: 222,325

[22] Filed: Apr. 4, 1994

Related U.S. Application Data

[63] Continuation of Ser. No. 995,588, Dec. 22, 1992, abandoned.

[30] Foreign Application Priority Data

Dec. 24, 1991 [DE] Germany .................. 41 43 021.2

[51] Int. Cl.$^6$ ................ C07C 1/00; C07C 2/66; C07C 15/46
[52] U.S. Cl. .......... 585/438; 585/435; 585/452; 585/454; 585/469
[58] Field of Search ............... 585/435, 436, 585/438, 452, 453, 454, 457, 469

[56] References Cited

U.S. PATENT DOCUMENTS 4,670,579  6/1987  Davidson .................. 560/83

OTHER PUBLICATIONS

Kikukawa, K., et al, *Chem. Lett.*: 159–162 (1977).
Kikukawa, K., et al, *Bull. Chem. Soc. Jpn.* 52:2609–2610.
Akiyama, F., et al, *J. Org. Chem* 45:2359–2361 (1980).
Kikukawa, K., et al, *J. Org. Chem.* 46:4885–4888 (1981).
Kikukawa, K., *Tetrahedron* 37:31–36 (1981).

*Primary Examiner*—P. Achutamurthy
*Attorney, Agent, or Firm*—Connolly and Hutz

[57]  ABSTRACT

The present invention relates to a process for preparing vinyl-substituted aromatic compounds of the formula (I) Ar—CH=CH$_2$, where Ar is a phenyl group that may bear 1 to 5 substituents, naphthyl or anthryl or a naphthyl radical bearing 1 to 7 substituents or an anthryl radical bearing 1 to 8 substituents, or a mononuclear five-, six- or seven-membered heterocyclic aromatic group which contains an oxygen atom and/or one or two nitrogen atoms in the ring and may bear 1 to 5 substituents, wherein an arylamine of the formula (II) Ar—NH$_2$, where Ar has the aforementioned meaning, is reacted in an organic acid with an organic nitrite of the formula (III) R—ONO, where R is an alkyl group having 1 to 18 carbon atoms, a phenyl radical which may bear 1 to 3 alkyl groups each having 1 to 4 carbon atoms, or is an alkylcarbonyl group having 2 to 5 carbon atoms, and ethylene in an organic solvent in the presence of a palladium(0) of palladium(II) compound at temperatures of 0° to 35° C.

21 Claims, No Drawings

PROCESS FOR PREPARING VINYL-SUBSTITUTED AROMATIC COMPOUNDS FROM ARYLAMINES

This is a continuation of application Ser. No. 07/995,588, filed Dec. 22, 1992, abandoned.

DESCRIPTION

Process for preparing vinyl-substituted aromatic compounds from arylamines

The present invention relates to a process for preparing vinyl-substituted aromatic compounds by catalytic arylation of ethylene using arylamines.

Vinyl-substituted aromatic compounds are important monomers for the synthesis of polymers and constitute important intermediates for the preparation of pharmaceuticals and agrochemicals.

The conventional methods for preparing styrene and its derivatives, such as dehydrogenation of alkylaromatic compounds or the elimination of the corresponding alcohols, generally take place under drastic reaction conditions, are often insufficiently selective, or start from poorly accessible starting materials, and are therefore unsuitable for the industrial production of many functionalized styrenes.

It is known that diazonium salts react with ethylene under pressure and in the presence of palladium bisbenzylidene catalysts to form styrenes (Bull. Chem. Soc. Jpn. 52, (1979), p. 2609; Tetrahedron 37 (1981), p. 31). In this connection it is however necessary to operate with a large excess of basic salts and under pressure (6 to 8 atm. of ethylene). Furthermore, the diazonium salts to be employed have to be prepared separately from the corresponding amines, which is technically disadvantageous.

It is also known to react arylamines with liquid olefins in a palladium-catalyzed reaction in the presence of acids and tert.-butyl nitrite (Chem. Lett. (1977), p. 159; J. Org. Chem. 46 (1981), p. 4885). In this process mixtures of acids, such as chloroacetic acid and acetic acid, are generally used as solvent. The described reaction temperatures of 50° C. are not very suitable for sensitive substrates, such as functionalized styrenes. Reactive α,β-unsaturated carbonyl compounds, such as acrylic esters, and high boiling point inactive olefins, such as cyclohexene or 1-hexene and styrene, are mentioned as starting compounds. The process described in J. Org. Chem. 46 (1981), p. 4885 affords lower yields for nonactivated olefins than for activated alkenes. The preparation of vinyl-substituted aromatic compounds is not described.

Arylations of olefins using arylamines and tert.-butyl nitrite with addition of palladium(II) acetate have also been mentioned in J. Org. Chem. 45 (1980), p. 2359. In this connection however stoichiometric amounts of the expensive palladium compound are used, and the reaction cannot be successfully performed catalytically. Also, the yields are unsatisfactory. This method is therefore unsuitable for the industrial production of relatively large amounts of material.

A common feature of all the described methods is that they are carried out under typical organometallic protective gas conditions (nitrogen or argon inert atmosphere), which involves additional complexity of the apparatus and complicates the industrial implementation of the method.

The object of the present invention was to provide a process for the catalytic preparation of vinyl-substituted aromatic compounds by arylation of ethylene using arylamines that does not have the aforedescribed disadvantages and that affords in a simple manner in particular the vinyl-substituted aromatic compounds in the highest possible yield and without interfering impurities.

This object can surprisingly be successfully achieved according to the invention by a process for preparing vinyl-substituted aromatic compounds of the formula (I) Ar—CH=CH$_2$, where Ar is a phenyl group that may bear 1 to 5 substituents, naphthyl or anthryl or a naphthyl radical bearing 1 to 7 substituents or an anthryl radical bearing 1 to 8 substituents, or a mononuclear five-, six- or seven-membered heterocyclic aromatic group which contains an oxygen atom and/or one or two nitrogen atoms in the ring and may bear 1 to 5 substituents, wherein an arylamine of the formula (II) Ar—NH$_2$, where Ar has the aforementioned meaning, is reacted in an organic acid with an organic nitrite of the formula (III) R—ONO, where R is an alkyl group having 1 to 18 carbon atoms, a phenyl radical, which may bear 1 to 3 alkyl groups each having 1 to 4 carbon atoms, or is an alkylcarbonyl group having 2 to 5 carbon atoms, and ethylene in an organic solvent in the presence of a palladium(0) of palladium(II) compound at temperatures of 0° to 35° C.

The substituents in the Ar radical are identical or different and are preferably a non-aromatic hydrocarbon radical having 1 to 8 carbon atoms, in particular having 1 to 4 carbon atoms, but particularly preferably methyl, an alkoxy or alkylthio radical having in each case 1 to 8 carbon atoms, aryl or aryloxy radical having in each case 6 to 14 carbon atoms, a —OCOR—, —COOR—, —COR—, —OSiR$_3$—, —NHCOR—, —NR$_2$—, —PR$_2$—, —PO$_2$R—, —PO$_3$R—, —SOR—, —SO$_2$R— or —SO$_3$R—group, where R is in each case hydrogen, alkyl having 1 to 12 carbon atoms, preferably having 1 to 6 carbon atoms, particularly preferably having 1 to 4 carbon atoms, and/or aryl having 6–10 carbon atoms, or is a —OH, —CN, —NO or —NO$_2$ group or halogen, in particular fluorine, chlorine or bromine. The term alkyl is in this connection also intended to include in each case cycloalkyl.

Organic nitrites of the formula (III) which can be employed are, for example, methyl, ethyl, n- or i-propyl nitrites, the various butyl, pentyl, hexyl or octyl nitrites, benzoyl nitrite, phenyl nitrite, o-, m- and p-methylphenyl nitrite, acetyl nitrite and propionyl nitrite, though mixtures of various organic nitrites are also suitable. Alkyl nitrites such as tert.-butyl or amyl nitrite are preferred. The nitrite is expediently used in a 0.5 to 10, preferably a 0.7 to 5, particularly preferably a 1 to 2 fold molar amount with respect to the arylamine (II).

Examples of suitable compounds of the formula (II) are the following: aniline, which may be substituted in the o-, m- or p-position by methyl, ethyl, n-propyl, i-propyl, n-butyl, i-butyl, tert.-butyl, fluorine, chlorine, bromine, iodine, hydroxyl, benzyloxy or acetoxy, and aminoacetophenone, aminoanthraquinone, aminoazobenzene, aminobenzamide, 2-aminobenzimidazole, aminobenzoic acid, aminobenzenephosphonic acid, aminobenzotrifluoride, aminobenzyl alcohol, aminobiphenyl, 4-amino-2-chlorobenzoic acid, p-anisidine, 2-amino-3,5-dichloropyridine, aminodiphenyl ether, 2-amino-4-methoxy-5-nitroanisole, aminomethylbenzoic acid, aminomethylbenzyl alcohol, aminophenylboronic acid, aminophenylacetic acid, aminophthalic acid, aminopyrimidine, and trans-4-aminocinnamic acid hydrochloride. Preferred compounds of the formula (II) are aminomethylbenzene, aminomethoxybenzene, aminoacetoxybenzene, aminonitrobenzene, aminonitrotoluene, aminobenzoic acid, diaminobenzene, aminopyrimidine, aminomethylacetoxybenzene, phenyl p-aminopropionate, ethyl aminobenzoate, and aminobenzonitrile.

The organic acid is generally formic acid, acetic acid, propionic acid, trifluoroacetic acid or chloroacetic acid. Formic acid, propionic acid and chloroacetic acid are preferred, though acetic acid is particularly preferred. In general the acid is used in a 0.1 to 1000, preferably a 1 to 100, particularly preferably a 10 to 50 fold amount by weight with respect to the arylamine (II).

In general aprotic and protic organic solvents, with the exception of carboxylic acids, may be used as the organic solvent. The organic solvent is expediently added in a 0.1 to 500 fold, in particular a 1 to 100 fold amount by weight with respect to the arylamine (II). Suitable organic solvents are for example optionally chlorinated aliphatic, cycloaliphatic or aromatic hydrocarbons such as n-pentane, n-heptane, n-octane, cyclopentane, cyclohexane, benzene, toluene, xylenes and chlorobenzene; aromatic, aliphatic and cyclic ethers such as anisole, diethyl ether, di-isopropyl ether, tetrahydrofuran, methyltert.-butyl ether and dioxane; N-substituted morpholines, such as N-methylmorpholine and N-formylmorpholine; nitriles, particularly benzonitrile and alkylnitriles having 2 to 5 carbon atoms, such as propionitrile and butyronitrile; 3-methoxypropionitrile and 3-ethoxypropionitrile; dialkyl sulfoxides such as dimethyl and diethyl sulfoxide; N,N-dialkylamides of aliphatic monocarboxylic acids having 1 to 3 carbon atoms in the acid part, such as N,N-dimethylformamide and N,N-dimethylacetamide; alcohols having up to 8 carbon atoms, such as ethanol, n-propanol and tert.-butanol; aliphatic and cyclic ketones, such as acetone, diethyl ketone, methyl isopropyl ketone, cyclopentanone, cyclohexanone, 1,3-dimethyl-2-imidazolidinone and 1,3-dimethyl-3,4,5,6-tetrahydro-2-(1H)-pyrimidinone; tetramethylurea; esters, such as esters of carbonic acid, e.g. diethyl carbonate; nitromethane; alkyl or alkoxyalkyl esters of aliphatic monocarboxylic acids having a total of 2 to 8 carbon atoms, such as methyl, ethyl, n-butyl and isobutyl acetate, ethyl and n-butyl butyrate, and 1-acetoxy-2-ethoxyethane and 1-acetoxy-2-methoxyethane or triethyl phosphate. However, preferred solvents also include chlorinated aliphatic hydrocarbons, in particular dichloromethane and chloroform, and diethyl ether, tert.-butyl methyl ether, tetrahydrofuran, dioxane, ethanol, n-propanol, acetonitrile and tert.-butanol.

The palladium catalyst is expediently used in a 0.0001 to 1, preferably a 0.001 to 0.1, in particular a 0.01 to 0.08 fold molar amount with respect to the arylamine (II). Palladium catalysts include for example palladium(II) acetate, palladium(II) chloride, palladium(II) nitrate, tetrakis(triarylphosphine) palladium, palladium(II) trifluoroacetate, palladium(II) bromide, disodium tetrachloropalladate, bisdibenzylidene palladium(0) or trisdibenzylidenedipalladium. These catalysts may for example be supported on heterogeneous carriers such as activated charcoal, aluminum oxide, barium sulfate and calcium carbonate, though they may also be used directly as solids or as solutions in the aforementioned solvents.

However, the catalysts used are preferably palladium(II) acetate and palladium(0) on activated charcoal.

The process according to the invention is preferably carried out at temperatures of 15° to 30° C., in particular at 20° to 25° C. At higher temperatures the activity of the catalyst drops and secondary reactions occur. Particularly unreactive compounds may however still be satisfactorily converted even at higher temperatures.

The pressure at which the ethylene is metered in or at which the reaction is carried out is not crucial in the process according to the invention. It is however advantageous to pass ethylene or a mixture of ethylene with inert gases, for example nitrogen, argon or lower alkanes, for example ethane, at atmospheric pressure through the reaction solution or over the reaction solution. The reaction can however also be carried out at an ethylene excess pressure or under an excess pressure of the gas mixture. The pressure in this case is then 1 to 500 bar.

After completion of the reaction the reaction mixture is worked up in the conventional way, as described for example in J. Org. Chem. 46 (1981), p. 4885.

The process according to the invention is particularly surprising insofar as attempts to prepare vinyl-substituted aromatic compounds in a process similar to that published in J. Org. Chem. 46 (1981) p. 4885 only afforded unsatisfactory yields. For example, vinyl-substituted aromatic compounds are obtained only in a yield of less than 7% by this process at 50° C. and without the addition of an organic solvent (cf. Comparative Experiment 1). The yield can in each case be slightly improved by lowering the reaction temperature (Comparative Experiment 2) or by adding an organic solvent. However, the combination of these two reaction parameters surprisingly produces a synergistic improvement in the yield of the desired products.

Moreover, stilbenes are formed in relatively high yields from arylamines and styrenes by the process described in J. Org. Chem. 46 (1981) p. 4885. By comparison, styrenes surprisingly react only very slowly in the present process, which is why undesirable stilbenes are formed only in very small amounts of less than 5%. This further reaction to give stilbenes is also a problem in the Heck reaction of aryl halides with ethylene.

The process according to the invention enables the synthesis of vinyl-substituted aromatic compounds in one step under particularly mild conditions (low temperatures) and in a simple and efficient manner (no protective gas, low complexity of the apparatus). The low reaction temperatures are particularly advantageous in the preparation of more reactive styrenes.

In addition the present process is an ecologically exemplary process in which neither coupling products nor stoichiometric amounts of salt waste are formed.

In contrast to the reaction of diazonium salts with ethylene (Bull. Chem. Soc. Jpn. 52 (1979) p. 2609), the present process omits the isolation of the diazonium salt, which means that the process is technically substantially more simple to carry out. Also, the use of expensive chemicals such as tetrafluoroboric acid is avoided. Besides, secondary products which are difficult to separate, such as arylbutenes, are not formed.

The addition of an organic solvent is thus particularly advantageous since the service life of the active catalyst is increased and the working-up of the reaction mixture is simplified.

Examples 1. 50 ml of acetic acid were placed in a 500 ml three-necked flask equipped with stirrer, dropping funnel and internal thermometer, followed by 2 mmol of palladium acetate. 40 mmol of aniline were then added dropwise to the solution, during which procedure the internal temperature did not rise above 30° C. Ethylene was then passed into the solution and 45 mmol of tert.-butyl nitrite were added dropwise, during which procedure the internal temperature did not rise above 25° C. After the addition of 40 ml of dichloromethane, the reaction solution was stirred for 16 hours. Gas chromatography measurements showed a conversion of 80%. The yield of styrene was 69%, based on the amine employed.

2. Example 1 was repeated, except that 40 mmol of finely ground p-anisidine were added to the solution instead of aniline. Gas chromatography measurements showed a conversion of 85%. The yield of p-methoxystyrene was 72%, based on the amine employed.

3. Example 1 was repeated, except that 40 mmol of 2-fluoroaniline were added dropwise to the solution instead of aniline. Gas chromatography measurements showed a conversion of 87%. The yield of 2-fluorostyrene was 70%, based on the amine employed.

4. Example 1 was repeated, except that 40 mmol of 4-chloroaniline were added to the solution instead of aniline. Gas chromatography measurements showed a conversion of 84%. The yield of 4-chlorostyrene was 72%, based on the amine employed.

5. Example 1 was repeated, except that 40 mmol of 3-toluidine were added to the solution instead of aniline. Gas chromatography measurements showed a conversion of 83%. The yield of 3-methylstyrene was 66%, based on the amine employed.

6. 20 ml of acetic acid, 20 g of chloroacetic acid and 10 mmol of aniline were placed in a 500 ml three-necked flask equipped with stirrer, dropping funnel and internal thermometer, followed by 0.5 mmol of bis(dibenzylideneacetone)palladium. Following this ethylene was passed through the solution. A solution of 11 mmol of tert.-butyl nitrite in 10 ml of acetic acid was then added dropwise to the reaction solution at room temperature and within 15–20 minutes. 25 ml of ethanol were then added. After 16 hours gas chromatography measurements showed a conversion of 55%.

Comparaitive Example 1

20 ml of acetic acid, 20 g of chloroacetic acid and 10 mmol of aniline were placed in a 500 ml three-necked flask equipped with stirrer, dropping funnel and internal thermometer, and 0.5 mmol of bis(dibenzylideneacetone)palladium was added. Ethylene was then passed through the solution. A solution of 11 mmol of tert.-butyl nitrite in 10 ml of acetic acid was then added dropwise within 15–20 minutes to the reaction solution warmed to 50° C. After 16 hours gas chromatography measurements showed a conversion of 7%.

Comparitive Example 2

The same procedure as in Comparitive Example 1 was adopted, but the solution of tert.-butyl nitrite in acetic acid was added dropwise at room temperature. After 16 hours gas chromatography measurements showed a conversion of 15%.

We claim:

1. A process for preparing vinyl-substituted aromatic compounds of the formula (I) Ar—CH=CH$_2$, Ar being a phenyl group that optionally bears 1 to 5 substituents, naphthyl or anthryl or a naphthyl radical bearing 1 to 7 substituents or an anthryl radical bearing 1 to 8 substituents, or a mononuclear five-, six- or seven-membered heterocyclic aromatic group which contains an oxygen atom and/or one or two nitrogen atoms in the ring and optionally bears 1 to 5 substituents, wherein an arylamine of the formula (II) Ar—NH$_2$, where Ar has the aforementioned meaning, is reacted with an organic acid with an organic nitrite of the formula (III) R—ONO, where R is an alkyl group having 1 to 18 carbon atoms, a phenyl radical which optionally bears 1 to 3 alkyl groups each having 1 to 4 carbon atoms, or is an alkylcarbonyl group having 2 to 5 carbon atoms, and ethylene in an organic solvent in the presence of a palladium(0) or palladium(II) compound as a catalyst at temperatures of 0° to 35° C.

2. The process as claimed in claim 1, wherein the organic acid is an organic carboxylic acid, and wherein the substituents in the Ar radical are identical or different and are a non-aromatic hydrocarbon radical having 1 to 8 carbon atoms, an alkoxy or alkylthio radical having in each case 1 to 8 carbon atoms, aryl or aryloxy having in each case 6 to 14 carbon atoms, a —OCOR—, —COOR—, —COR—, —OSiR$_3$—, —NHCOR—, —NR$_2$—, —PR$_2$—, —PO$_2$R—, —PO$_3$R—, —SOR—, —SO$_2$R—or —SO$_3$R—group, where R is in each case independently hydrogen, alkyl having 1 to 12 carbon atoms, aryl having 6–10 carbon atoms, or is a —OH, —CN, —NO or —NO$_2$ group or halogen.

3. The process as claimed in claim 1, wherein the organic solvent is a chlorinated aliphatic hydrocarbon, diethyl ether, tert-butyl methyl ether, tetrahydrofuran, dioxane, ethanol, n-propanol, acetonitrile or tert-butanol.

4. The process as claimed in claim 1, wherein the organic solvent is used in a 0.1 to 500, fold amount by weight with respect to the arylamine.

5. The process as claimed in claim 1, wherein the organic nitrite is an alkyl nitrite.

6. The process as claimed in claim 5, wherein the alkyl nitrite is tert-butyl or amyl nitrite.

7. The process as claimed in claim 1, wherein the organic nitrite is used in a 0.5 to 10 fold molar amount with respect to the arylamine.

8. The process as claimed in claim 1, wherein the arylamine of the formula (II) is aminomethylbenzene, aminomethoxybenzene, aminoacetoxybenzene, aminonitrobenzene, aminonitrotoluene, aminobenzoic acid, diaminobenzene, aminopyrimidine, aminomethylacetoxybenzene, phenyl p-aminopropionate, ethyl aminobenzoate or aminobenzonitrile.

9. The process as claimed in claim 1, wherein the organic acid is formic acid, acetic acid, propionic acid or chloroacetic acid.

10. The process as claimed in claim 1, wherein the organic acid is used in a 0.1 to 1000 fold amount by weight with respect to the arylamine.

11. The process as claimed in claim 1, wherein palladium(II) acetate or palladium(0) on activated charcoal is used as a catalyst.

12. The process as claimed in claim 1, wherein the catalyst is used in a 0.0001 to 1 fold molar amount with respect to the arylamine.

13. The process as claimed in claim 1, wherein the process is carried out at temperatures of 15° to 30° C., 14. The process as claimed in claim 1, wherein the ethylene is used alone or as a mixture with inert gases.

15. The process as claimed in claim 14, wherein the inert gas is nitrogen, argon or a lower alkane.

16. The process as claimed in claim 1, wherein the ethylene or the mixture of ethylene with inert gases is passed into the reaction mixture at a pressure of 1 to 500 bar.

17. The process as claimed in claim 2, wherein said non-aromatic hydrocarbon radical has 1 to 4 carbon atoms, R is hydrogen or alkyl having 1 to 4 carbon atoms, and said halogen is fluorine, chlorine, or bromine.

18. The process as claimed in claim 1, wherein the organic solvent is used in a 1 to 100 fold amount by weight with respect to the arylamine, the organic nitrite is used in a 0.7 to 5 fold molar amount with respect to the arylamine;

the organic acid is used in a 1 to 100 fold amount by weight with respect to the arylamine;

the catalyst is used in a 0.001 to 0.1 fold molar amount with respect to the arylamine; and the process is carried out at temperatures of 20° to 25° C.

19. The process as claimed in claim 18, wherein, with respect to the arylamine:

said amount of organic nitrite is a 1 to 2 fold molar amount;

said amount of organic acid is a 10 to 50 fold amount by weight; and said amount of catalyst is a 0.01 to 0.08 fold molar amount.

20. The process as claimed in claim 2, wherein the organic carboxylic acid is formic acid, acetic acid, propionic acid, trifluoroacetic acid or chloroacetic acid.

21. A process for the preparation of vinyl-substituted aromatic compounds of the formula Ar—CH=CH$_2$, where Ar is a phenol group which optionally bears 1 to 5 substituents, naphthyl or anthryl radical bearing 1 to 7 substituents or an anthryl radical bearing 1 to 8 substituents, or a mononuclear five-, six- or seven-membered heterocyclic aromatic groups which contains an oxygen atom and/or one to two nitrogen atoms in the ring and optionally bears 1 to 5 substituents, comprising the steps of reacting an arylamine of the formula (II) Ar—NH$_2$, where Ar is as defined above, with an organic nitrate of the formula (III) R—ONO, where R is an alkyl group having 1 to 18 carbon atoms, a phenyl radical which optionally bears 1 to 3 alkyl groups each having 1 to 4 carbon atoms, or is an alkyl carbonyl group having 2 to 5 carbon atoms, in an organic carboxylic acid, and with ethylene, in an organic solvent selected from the group consisting of chlorinated aliphatic hydrocarbon, diethyl ether, tert-butyl methyl ether, tetrahydrofuran, dioxane, ethanol, n-propanol, acetonitrile or tert-butanol, in the presence of a palladium (0) or a palladium (II) compound as catalysts, at temperatures of from 0° to 35° C.

* * * * *

UNITED STATES PATENT AND TRADEMARK OFFICE
CERTIFICATE OF CORRECTION

PATENT NO. : 5,475,176
DATED : December 12, 1995
INVENTOR(S) : Matthias Beller and Heinz Strutz It is certified that error appears in the above-indentified patent and that said Letters Patent is hereby corrected as shown below:

In claim 21 (column 8, line 10), "nitrate" should read --nitrite--.

Signed and Sealed this

Fourteenth Day of May, 1996

Attest:

BRUCE LEHMAN

*Attesting Officer*     *Commissioner of Patents and Trademarks*